United States Patent [19]

McCarthy

[11] Patent Number: 4,997,983

[45] Date of Patent: Mar. 5, 1991

[54] PROCESS FOR PRODUCTION OF IOVERSOL

[75] Inventor: William Z. McCarthy, St. Louis, Mo.

[73] Assignee: Mallinckrodt, Inc., St. Louis, Mo.

[21] Appl. No.: 472,691

[22] Filed: Jan. 31, 1990

[51] Int. Cl.$^5$ .................. C07C 233/00; C07C 235/00; C07C 237/00; C07C 239/00

[52] U.S. Cl. ........................................ 564/153; 424/5; 564/156

[58] Field of Search ............... 564/153, 156; 424/5

[56] References Cited

U.S. PATENT DOCUMENTS

| | | | |
|---|---|---|---|
| 3,701,771 | 10/1972 | Almen et al. | 424/5 |
| 4,001,323 | 1/1977 | Felder et al. | 424/5 |
| 4,021,481 | 5/1977 | Almen et al. | 424/5 |
| 4,250,113 | 2/1981 | Nordal et al. | 424/5 |
| 4,364,921 | 12/1982 | Speck et al. | 424/5 |
| 4,396,598 | 8/1983 | Lin | 424/5 |

FOREIGN PATENT DOCUMENTS 1198739 12/1985 Canada ........................ 424/5

*Primary Examiner*—Glennon H. Hollrah
*Assistant Examiner*—Scott C. Rand
*Attorney, Agent, or Firm*—Rita E. Downard; Roy J. Klostermann

[57] ABSTRACT

A process for the production of N,N'-bis(2,3-dihydroxypropyl)-5-N-(2-hydroxyethyl)glycolamido-2,4,6-triiodoisopht alamide wherein a mixture of 1,1,2-trichloroethane and 5-[(N-(2-acetoxyethyl)acetoxyacetamido]N,N'-bis(2,3-diacetoxypropyl)-2,4,6-triiodoisophthalamide (hexaacetate) is distilled to remove 1,1,2-trichloroethane, at least a part of which is distilled as an azeotrope with water, so that a solvent exchange is effected to produce a mixture of hexaacetate in water. Hydrolysis of hexaacetate produces the desired product.

11 Claims, No Drawings

PROCESS FOR PRODUCTION OF IOVERSOL

FIELD OF THE INVENTION

This invention relates to a process for the preparation of N,N'-bis(2,3-dihydroxypropyl)-5-N-(2-hydroxyethyl) glycolamido-2,4,6-triiodoisophthalamide, hereinafter called by its generic name, ioversol.

BACKGROUND OF THE INVENTION

Ioversol was disclosed as useful as a nonionic x-ray contrast agent in U.S. Pat. No. 4,396,598. An intermediate in its production is 5-[N-(2-acetoxyethyl)acetoxyacetamido]-N,N'-bis (2,3-diacetoxypropyl)-2,4,6-triiodoisophthalamide, hereinafter "hexaacetate", having the following structure:

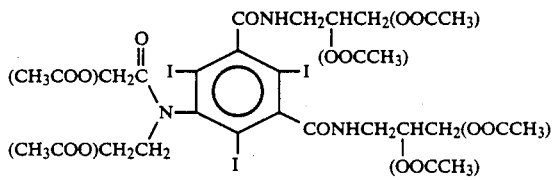

This compound and its use in producing ioversol are disclosed in Canadian Patent No. 1,198,739, incorporated herein by reference. Hexaacetate, as disclosed therein, may be produced by alkylating a compound of the formula:

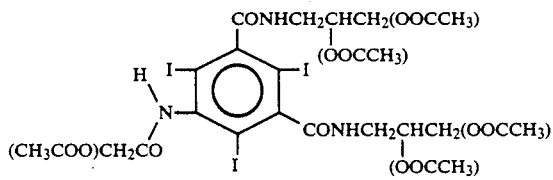

with a compound of the formula:

wherein X is halogen or another leaving group, to produce hexaacetate and then hydrolyzing hexaacetate to produce ioversol.

The alkylation procedure may be carried out in the presence of a base, for example sodium methoxide, sodium ethoxide, sodium hydride, sodium carbonate or potassium carbonate. The reaction may also be carried out in the presence of a diluent or solvent such as methanol, ethanol, dimethylsulfoxide (DMSO), dimethylacetamide (DMAC) or propylene glycol. The alkylating agent may be 2-bromoethyl acetate, for example.

The hydrolyzing procedure may be carried out by use of a hydrolyzing agent which may be, for example, sodium methoxide in methanol, ammonia in methanol, trifluoroacetic acid in aqueous methanol, aqueous sodium carbonate, aqueous sodium hydroxide, aqueous potassium hydroxide, aqueous hydrochloric acid, or aqueous hydrobromic acid; or by use of an ion exchange resin in the presence of water, such as an Amberlite ® resin, for example Amberlite ® IR-120 HCP resin.

This procedure has heretofore required isolation and crystallization of substantially pure hexaacetate prior to the hydrolysis step. This has typically been accomplished by the addition of 1,1,2-trichloroethane (TCE) to the "hexaacetate"/DMSO mixture followed by extraction with water to remove DMSO and certain impurities. Some of the TCE is removed by distillation to concentrate the resulting "hexaacetate"/TCE mixture. Amyl acetate is then added, causing "hexaacetate" to crystallize. The crystals are filtered out and dried. This necessitated the use of expensive drying equipment and resulted in appreciable product losses due to less than complete crystallizations.

An alternative method that would eliminate the need for isolation and crystallization, avoiding the need for amyl acetate, and allow hydrolysis to be performed on hexaacetate at higher yields was desired. It is an object of the present invention to meet these needs.

SUMMARY OF THE INVENTION

5-[N-(2-acetoxyethyl)acetoxyacetamido]-N,N'-bis (2,3-diacetoxypropyl)-2,4,6-triiodoisophthalamide (hexaacetate) is produced by alkylation of 5-acetoxyacetamido-N,N'-bis (2,3-diacetoxypropyl)-2,4,6-triiodoisophthalamide by 2-bromoethyl acetate in the presence of a base, such as potassium carbonate, in an organic solvent, such as DMSO. The by-products and solvent are removed from the reaction mixture by adding 1,1,2-trichloroethane (TCE) and extracting the mixture with water. The TCE is removed from hexaacetate by distillation, at least in part as an azeotrope with water. A hydrolyzing agent miscible with water is then added to remove the acetate groups and produce ioversol.

This process has the advantage of not requiring isolation of hexaacetate from TCE by crystallization, thus eliminating the need for amyl acetate addition and the drying step. It also has the advantage of removing substantially all of the TCE by replacement with water, the preferred medium for the hydrolysis step. The TCE distillate is easily collectable and, if desired, recyclable. Elimination of the drying step eliminates the capital cost of a dryer and the attendant safety and environmental problems caused by chlorinated solvent vapor emitted from such a dryer.

DETAILED DESCRIPTION OF THE INVENTION

5-Acetoxyacetamido-N,N'-bis(2,3-diacetoxypropyl)2,4,6-triiodoisophthalamide, as disclosed in Canadian Patent No. 1,198,739, discussed above, may be prepared generally by reacting 5-amino-2,4,6-triiodoisophthaloyl chloride with 3-amino-1,2-propanediol; reacting the product of that reaction with acetic anhydride, and finally reacting that product with acetoxyacetyl chloride.

This compound may then be alkylated at the 5-N position by reaction with 2-bromoethyl acetate. This reaction is carried out in the presence of a base as discussed above, and in an organic solvent capable of dissolving or suspending the reactants and base, preferably DMSO. The reaction results in a bromide by-product, which is be removed along with unreacted base and the reaction solvent by adding 1,1,2-trichloroethane (TCE) and extracting the mixture with water. Preferably the water wash is followed by washings with successively more concentrated sodium chloride solutions, for example, 5 percent aqueous sodium chloride, followed by 10 percent aqueous sodium chloride washes until the solvent and byproduct levels are acceptably low. For DMSO, for example, the acceptable level is less than 10 ppm. This usually results in a mixture of hexaacetate in TCE at approximately 25 to 30% solids.

In order to remove the TCE and provide an aqueous mixture of hexaacetate as preferred for the hydrolysis step, the present invention provides for a solvent exchange. This is accomplished by distilling off the TCE and adding water at some point prior to or during the distillation so that at least the last part of the TCE is distilled as an azeotrope with water.

The azeotrope distillation may be achieved in various ways. Water may be added to the TCE-hexaacetate mixture prior to beginning distillation so that essentially all of the TCE is distilled as an azeotrope. Alternatively, distillation may be begun prior to addition of water, and part of the TCE is distilled separately. Water is then added and the remainder of the TCE is distilled as an azeotrope. Preferably, more than half of the volume of TCE is removed prior to the water addition.

The amount of water added thus depends on the point at which it is to be added. The minimum amount needed may be calculated by determining the amounts required to produce a mixture of hexaacetate in water containing between 20 and 30% solids, preferably between 20 and 25% solids, plus the amount needed to azeotrope with the TCE. The latter amount is calculated by multiplying the volume of TCE remaining by 0.2. It is preferred that an amount slightly more than the calculated minimum be used. Approximately 1.5 times the minimum amount has been found to be preferred.

The total amount of water may be added all at once or in increments, but is preferably added continuously during the distillation. The addition may be controlled by use of a level indicator in the distillation vessel so as to maintain the calculated desired level during distillation.

The pot temperature of the distillation should be at about the minimum needed to induce distillation of TCE of a TCE-water azeotrope. This is between 50° and 100° C., preferably between 52° and 84° C. A vacuum may be established to lower the minimum temperature required. A vacuum may be used when TCE alone is being distilled and atmospheric pressure restored when water is added and during the azeotropic distillation. Alternatively, the entire distillation may be performed under vacuum. Preferably, a vacuum is used if part of the TCE is distilled off prior to any water addition.

The azeotrope distillate may be checked periodically to determine the extent of TCE removal. The solvent exchange is complete when the distillate is not two-phase, i.e., the distillate is essentially all water.

The goal of the exchange is to remove essentially all of the TCE so that the aqueous hexaacetate distillation "residue" contains less than 10 ppm TCE. This may be determined by analysis by GC or other appropriate method.

When the exchange is complete and the distillation is stopped, a hydrolyzing agent is added to produce ioversol. Any hydrolyzing agent that is miscible or soluble in the aqueous medium and will not adversely affect the stability of ioversol may be used. Examples are sodium methoxide in methanol, ammonia in methanol, trifluoroacetic acid in aqueous methanol, aqueous sodium carbonate, aqueous sodium hydroxide, aqueous potassium hydroxide, aqueous hydrochloric acid, sulfuric acid, or aqueous hydrobromic acid; or by use of an ion exchange resin in the presence of water, such as an Amberlite ® resin, for example Amberlite ® IR-120 HCP resin.

Preferably the hydrolyzing agent is an acid, more preferably sulfuric acid.

Some hydrolysis of hexaacetate will have occurred during distillation after the addition of the water. The extent of hydrolysis will vary with temperature and length of time water is present. However, this hydrolysis will generally not proceed to a great degree. If sulfuric acid is used to complete the hydrolysis, approximately 0.1 moles should be used per mole of hexaacetate.

The present invention is illustrated by the following example, but is not limited thereby.

EXAMPLE

One liter of 1,1,2-trichloroethane (TCE), 1485 g, containing 481 g 5-[N-(2-acetoxyethyl)acetoxyacetamido]-N,N'-bis (2,3-diacetoxypropyl)-2,4,6-triiodoisophthalamide (hexaacetate) was placed in a 3-neck round bottom flask equipped with a water-addition reservoir, a stirrer, a thermometer, and a vacuum/condenser and receiver apparatus. The flask was placed in a hot water bath, initially held at 50° C. 100 mL water were added to the flask with stirring. A vacuum equal to 25 inches (125 mmHg) was established. The temperature of the water bath was slowly raised to 60° C. and distillation started. The rate was slow so the bath temperature was raised to 70° C. and the vacuum to 26 in (b 100 mmHg). A good rate of distillation was achieved so three 100-mL aliquots of water were added over 17 minutes. After 10 minutes more, the heat and vacuum were removed. The distillate at that point was 80 mL water and 170 mL TCE, equal to 25% water by weight.

The distillation was restarted and an additional five 100-mL aliquots of water were added over one hour. As distillation slowed, the water bath temperature was raised to 84° C. The distillation cut was 89% water at that point. When the distillate no longer separated into two layers, the distillation was stopped. The distillate totaled 600 mL: 315 mL TCE and 285 mL water, equal to 48% w/v water. The distillation residue contained less than 30 ppm TCE.

The residue was mixed with 4.7 g $H_2SO_4$ (0.107 molepercent) with stirring and heating. After 1½ hours, the mixture was homogenous, and assay by HPLC showed less than 2% unreacted hexaacetate. After four hours, analysis showed the hydrolysis to be complete. The crude ioversol assayed at 94.3% purity.

What is claimed is:

1. A process for the production of ioversol from 5-[N-(2-acetoxyethyl) acetoxyacetamido]-N,N'-bis(2,3-diacetoxypropyl)-2,4,6-triiodoisophthalamide wherein said 5-[N-(2-acetoxyethyl)acetoxyacetamido-N,N'-bis (2,3-diacetoxypropyl)-2,4,6-triiodoisophthalamide is contained in a reaction medium from the alkylation of 5-acetoxyacetamido-N,N'-bis(2,3-diacetoxypropyl-2,4,6-triiodoisophthalamide by 2-bromoethyl acetate in an organic solvent, comprising the steps of:
   a. removing said organic solvent by adding 1,1,2-trichloroethane and washing the resulting mixture with water or aqueous sodium chloride solutions or both;
   b. distiling the mixture of 5-[N-(2-acetoxyethyl) acetoxyacetamido]-N,N'-bis(2,3-diacetoxypropyl)-2,4,6-triiodoisophthalamide in 1,1,2-trichloroethane until said 1,1,2-trichloroethane is distilled off, wherein at least part of said 1,1,2-trichloroethane is distilled off as an azeotrope with water, and c. thereafter, adding a hydrolyzing agent to the resulting aqueous distillation residue in an amount sufficient to substantially complete hydrolysis of said 5-[N-(2-acetoxyethyl) acetoxyacetamido]-N,N'-bis(2,3-diacetoxypropyl)-2,4,6-triiodoisophthalamide to produce ioversol.

2. The process of claim 1, wherein water is added to said mixture of 5-[N-(2-acetoxyethyl)acetoxyacetamido]-N,N'-bis (2,3-diacetoxypropyl)-2,4,6-triiodoisophthalamide in 1,1,2-trichloroethane before beginning distillation whereby substantially all of said 1,1,2-trichloroethane is distilled as an azeotrope with water.

3. The process of claim 1 wherein a portion of said 1,1,2-trichloroethane is distilled before addition of water to produce an azeotrope.

4. The process of claim 3, wherein at least half of said 1,1,2-trichloroethane is distilled before addition of water to produce an azeotrope distillation.

5. The process of claim 1, wherein said distillation is carried out at between 52° and 84° C.

6. The process of claim 1, wherein at least part of the distillation step is carried out under vacuum.

7. The process of claim 6, wherein substantially the whole distillation step is carried out under vacuum.

8. The process of claim 6 or 7, wherein said vacuum is between 125 and 75 mmHg.

9. The process of claim 1, wherein said hydrolyzing agent is selected from a group consisting of sulfuric acid, hydrobromic acid, and hydrochloric acid.

10. The process of claim 9, wherein said hydrolyzing agent is sulfuric acid.

11. The process of claim 1, wherein said organic solvent is dimethylsulfoxide.

* * * * *